United States Patent
Wang et al.

(10) Patent No.: US 12,217,857 B2
(45) Date of Patent: Feb. 4, 2025

(54) PUBLIC EVENT ADMINISTRATING SYSTEM

(71) Applicants: BEIJING BOE HEALTH TECHNOLOGY CO., LTD., Beijing (CN); BOE TECHNOLOGY GROUP CO., LTD., Beijing (CN)

(72) Inventors: Hongliang Wang, Beijing (CN); Yanyang Hu, Beijing (CN); Fang Zhai, Beijing (CN); Guoqiang Zhang, Beijing (CN); Yubin Zhou, Beijing (CN); Fuchen Tian, Beijing (CN); Lan Jiang, Beijing (CN)

(73) Assignees: BEIJING BOE HEALTH TECHNOLOGY CO., LTD., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 653 days.

(21) Appl. No.: 17/426,727

(22) PCT Filed: Feb. 28, 2020

(86) PCT No.: PCT/CN2020/077197
§ 371 (c)(1),
(2) Date: Jul. 29, 2021

(87) PCT Pub. No.: WO2021/168796
PCT Pub. Date: Sep. 2, 2021

(65) Prior Publication Data
US 2022/0319679 A1    Oct. 6, 2022

(51) Int. Cl.
*G16H 40/20*    (2018.01)
*A61B 5/00*    (2006.01)
*G06Q 10/0631*    (2023.01)

(52) U.S. Cl.
CPC ......... *G16H 40/20* (2018.01); *A61B 5/0022* (2013.01); *A61B 5/7465* (2013.01); *G06Q 10/06315* (2013.01)

(58) Field of Classification Search
CPC .... G16H 40/20; A61B 5/0022; A61B 5/7465; A61B 5/6826; A61B 5/6887; A61B 5/01;
(Continued)

(56) References Cited

U.S. PATENT DOCUMENTS

| 2007/0203742 | A1 | 8/2007 | Jones et al. |
| 2011/0066002 | A1 | 3/2011 | Clawson |

(Continued)

FOREIGN PATENT DOCUMENTS

| CN | 101231662 A | 7/2008 |
| CN | 104301397 A | 1/2015 |

(Continued)

OTHER PUBLICATIONS

Dickson K. W. Chiu et al., "Alert based disaster notification and resource allocation" Inf Syst Front (2010) pp. 12:29) to 12:47; Springer Science + Business Media LLC 2009; Published Mar. 20, 2009 (Year: 2009).*

(Continued)

*Primary Examiner* — Linh Giang Le
(74) *Attorney, Agent, or Firm* — Dilworth & Barrese, LLP.; Michael J. Musella, Esq.

(57) ABSTRACT

A public event administrating system is disclosed. The public event involves a plurality of individuals and the administrating system includes: a data collecting module, a data processing module, a medical resource scheduling module, and a grid administrating module. The data collecting module is configured to acquire initial data about the public event from a plurality of data sources. The data processing module is configured to process the initial data to (Continued)

acquire processed data. The medical resource scheduling module is configured to receive an individual service request and allocate currently available medical resources to an individual requesting service at least according to the individual service request. And, the grid administrating module is configured to divide a geographic region managed by the administrating system into a plurality of grids, and assign a plurality of grid administrators to the plurality of grids to respectively administrate individuals in the plurality of grids.

20 Claims, 9 Drawing Sheets

(58) Field of Classification Search
CPC . A61B 5/14551; A61B 5/6802; A61B 5/7282; G06Q 10/06315; G06Q 10/00; H04W 4/90
See application file for complete search history.

(56) References Cited

U.S. PATENT DOCUMENTS

2012/0123789 A1* 5/2012 Patel .................. G16H 40/20 705/2
2017/0323398 A1 11/2017 Dintenfass et al.

FOREIGN PATENT DOCUMENTS

| CN | 105740322 A | 7/2016 | |
|---|---|---|---|
| CN | 108345969 A | 7/2018 | |
| CN | 108498080 A | 9/2018 | |
| WO | WO-0219246 A2 * | 3/2002 | ........... G06F 19/321 |

OTHER PUBLICATIONS

Brownstine, JS; HealthMap, the development of automated real-time internet surveillance for epidemic intelligence; Internet Citation Nov. 29, 2007; pp. 1-3.

Extended European Search Report mailed Mar. 20, 2023 in application No. 20921676.1.

Dickson K. W. Chiu et al., "Alert based disaster notification and resource allocation" Inf Syst Front (2010) pp. 12:29 to 12:47; Springer Science + Business Media LLC 2009; as cited in the European Office Action in Application No. 20921676.1; Mailing Date: Dec. 12, 2023; Published Mar. 20, 2009.

Extended European Search Report mailed Dec. 12, 2023 in application No. 20921676.1-1218.

Chinese Office Action mailed May 30, 2024 in Application No. 202080000206.8.

* cited by examiner

FIG. 3

PUBLIC EVENT ADMINISTRATING SYSTEM

TECHNICAL FIELD

Embodiments of the present disclosure relate to a public event administrating system.

BACKGROUND

Emergent public events refer to emergent events that occur suddenly, causing or likely to cause heavy casualties, property losses, ecological environmental damage, and serious social harm, endangering public safety. The emergent public events generally include natural disasters, accident disasters, emergent public health events, and emergent social security events, etc. The emergent public health events mainly include infectious disease epidemics, mass diseases with unknown causes, food safety and occupational hazards, animal epidemics, and other events that seriously affect public health and life safety.

SUMMARY

At least one embodiment of the present disclosure provides a public event administrating system. The public event involves a plurality of individuals and the administrating system includes a data collecting module, a data processing module, a medical resource scheduling module, and a grid administrating module. The data collecting module is configured to acquire initial data about the public event from a plurality of data sources; the data processing module is configured to process the initial data to acquire processed data; the medical resource scheduling module is configured to receive an individual service request, and allocate currently available medical resources to an individual requesting service at least according to the individual service request; and the grid administrating module is configured to divide a geographic region managed by the administrating system into a plurality of grids, and assign a plurality of grid administrators to the plurality of grids to respectively administrate individuals in the plurality of grids.

For example, in at least one example of the public event administrating system, the initial data about the public event includes at least one of basic data, physical condition data, mobility data, or contact data of the plurality of individuals involved in the public event.

For example, in at least one example of the public event administrating system, the basic data includes at least one of address, age, gender, and identity number of an individual; the physical condition data includes at least one of clinical symptom data, physical sign data, or diagnosis result data; the mobility data includes travel history data; and the contact data includes at least one of data on whether the individual is in contact with an individual having an abnormal physical condition or data on whether the individual is in contact with an individual having a travel history in a predetermined geographic region.

For example, in at least one example of the public event administrating system, the public event administrating system further includes an individual information declaring module. The individual information declaring module is configured to allow an accessing individual to declare individual data; the individual data includes at least one of the basic data, the physical condition data, the mobility data, or the contact data; and the data collecting module is configured to acquire the individual data from the individual information declaring module as at least portion of the initial data about the public event.

For example, in at least one example of the public event administrating system, the data collecting module is further configured to acquire data from at least one of an online hospital admission data source, an offline hospital admission data source, an emergency rescue platform data source, or a physical sign monitoring device data source, the acquired data is served as at least portion of the initial data about the public event.

For example, in at least one example of the public event administrating system, the physical sign monitoring device data source communicates with a plurality of physical sign monitoring devices; and the plurality of physical sign monitoring devices include at least one of a body temperature detecting device provided in a public place, an instrument for monitoring patients provided in a hospital, or a wearable monitoring terminal.

For example, in at least one example of the public event administrating system, the grid administrating module includes a grid dividing sub-module and a grid administrator sub-module; the grid dividing sub-module is configured to divide the geographic region managed by the administrating system into the plurality of grids; and the grid administrator sub-module is configured to establish communication with the plurality of grid administrators respectively and is configured to respectively associate the plurality of individuals in the plurality of grids with the plurality of grids and respectively associate the plurality of individuals in the plurality of grids with the plurality of grid administrators, such that the plurality of grid administrators may respectively administrate the plurality of individuals in the plurality of grids.

For example, in at least one example of the public event administrating system, the grid administrating module is further configured to acquire the initial data about the public event from the data collecting module, and respectively supply the initial data about the public event to corresponding grid administrators.

For example, in at least one example of the public event administrating system, the processed data includes a list of abnormal individuals respectively belonging to the plurality of grids; the abnormal individual belongs to at least one of an individual having an abnormal physical condition, an individual having a travel history in a predetermined geographic region, an individual having been in contact with an individual having an abnormal physical condition, or an individual having been in contact with an individual having a travel history in the predetermined geographic region; and the grid administrating module is configured to acquire, from the data processing module, the list of abnormal individuals respectively belonging to the plurality of grids, and respectively supply the list of abnormal individuals respectively belonging to the plurality of grids to the plurality of grid administrators.

For example, in at least one example of the public event administrating system, the individual having an abnormal physical condition belongs to at least one of an individual having abnormal clinical symptom data, an individual having abnormal physical sign data, or an individual having an abnormal diagnosis result.

For example, in at least one example of the public event administrating system, the processed data includes a list of individuals respectively belonging to the plurality of grids who have not declared individual data within a predetermined time; the grid administrating module is configured to acquire, from the data processing module, the list of individuals respectively belonging to the plurality of grids who have not declared individual data within the predetermined time, and respectively supply the list of individuals respectively belonging to the plurality of grids who have not declared individual data within the predetermined time to the plurality of grid administrators.

For example, in at least one example of the public event administrating system, the grid administrator sub-module is further configured to respectively assign screening tasks to the plurality of grid administrators, and to acquire feedback information on the assigned screening tasks from the plurality of grid administrators.

For example, in at least one example of the public event administrating system, the administrating system further includes a grid administrator terminal module used in a terminal held by each of the plurality of grid administrators; and the grid administrator terminal module is further configured to communicate with the grid administrator sub-module, and is configured to allow each of the plurality of grid administrators to tag a specific individual in a grid administrated thereby and upload tag data.

For example, in at least one example of the public event administrating system, the processed data includes at least one of a statistical result of current physical conditions of the plurality of individuals involved in the public event, a trend of changes of focused individuals among the plurality of individuals involved in the public event, or a statistical result of regional distribution of focused individuals among the plurality of individuals involved in the public event; the statistical result of current physical conditions of the plurality of individuals involved in the public event includes at least one of a statistical result of current physical sign data of the plurality of individuals involved in the public event or a statistical result of current clinical symptom data of the plurality of individuals involved in the public event; and the focused individuals belong to at least one of confirmed individuals, suspected individuals, cured individuals, dead individuals, individuals in close contact with confirmed individuals, individuals under medical observation among the individuals in close contact with confirmed individuals, or individuals released from medical observation among the individuals in close contact with confirmed individuals.

For example, in at least one example of the public event administrating system, the medical resource scheduling module includes a hospital scheduling sub-module; the hospital scheduling sub-module is configured to allocate an offline admitting hospital to the individual requesting service, or to establish a connection between the individual requesting service and a hospital supplying online service, based on positioning data of the individual requesting service, admission amount of the hospital, and a physical condition of the individual requesting service.

For example, in at least one example of the public event administrating system, the medical resource scheduling module further includes an ambulance scheduling sub-module; the hospital scheduling sub-module is configured to allocate the offline admitting hospital to the individual requesting service; and the ambulance scheduling sub-module is configured to allocate an ambulance based on positioning data of the individual requesting service, distribution situation of offline admitting hospitals and currently available ambulances.

For example, in at least one example of the public event administrating system, the hospital scheduling sub-module is configured to establish the connection between the individual requesting service and the hospital supplying online service; and the hospital scheduling sub-module is further configured to acquire diagnostic data of the individual requesting service and supply the diagnostic data of the individual requesting service to the data collecting module.

For example, in at least one example of the public event administrating system, the public event administrating system further includes an information supplying module, wherein the information supplying module is configured to publish at least one of statistical results of focused individuals, protection knowledge, or rumor-refuting information; and the information supplying module is further configured to supply at least one of travel history information of confirmed individuals or medical resource information of a designated region.

For example, in at least one example of the public event administrating system, the administrating system further includes an individual service module used in an individual terminal, and the individual service module is configured to communicate with the medical resource scheduling module to send the individual service request and establish service connections.

For example, in at least one example of the public event administrating system, the individual service module is further configured to communicate with the grid administrating module to allow the individual service module to communicate with a grid administrator of a grid to which it belongs; and the individual service module is further configured to communicate with an individual information declaring module to allow the individual information declaring module to collect individual data.

BRIEF DESCRIPTION OF THE DRAWINGS

In order to explain the technical solutions of the embodiments of the present disclosure more clearly, the accompanying drawings of the embodiments will be briefly introduced below. Obviously, the accompanying drawings in the following description only refer to some embodiments of the present disclosure, rather than restrictions on the present disclosure.

FIG. 3 is a schematic diagram of an individual data collecting interface of an individual service module provided by at least one embodiment of the present disclosure;

DETAILED DESCRIPTION

Figure 1:
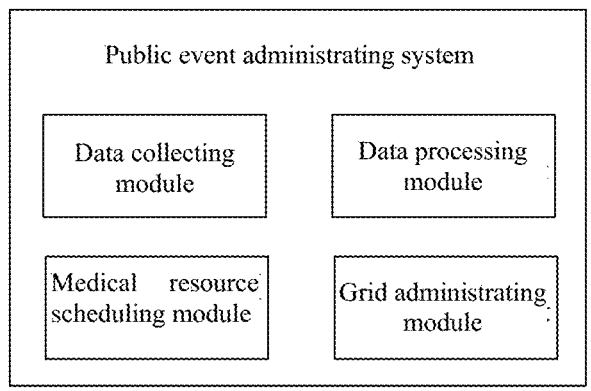
FIG. 1 is an exemplary block diagram of a public event administrating system provided by at least one embodiment of the present disclosure.

In order to make objects, technical solutions and advantages of the embodiments of the disclosure apparent, the technical solutions of the embodiments will be described clearly and completely in combination with the drawings related to the embodiments of the disclosure. Apparently, the described embodiments are part of the embodiments of the disclosure, rather than all of the embodiments. Based on the described embodiments herein, all other embodiments obtained by those skilled in the art without creative labor are within the protection scope of the present disclosure.

Unless otherwise defined, all the technical and scientific terms used herein shall have the usual meanings understood by those with ordinary skills in the field to which the present disclosure belongs. The terms "first", "second" and similar words used in the present disclosure are not intended to indicate any sequence, amount or importance, but are only used to distinguish various components. Also, the terms such as "a", "one" or "the" are not intended to limit the amount, but indicate the existence of at least one. The terms "comprise" or "include" are intended to specify that the elements or the objects stated before these terms encompass the elements or the objects and equivalents thereof listed after these terms, without excluding other elements or objects. The phrases "connect", "connected to", etc., are not limited to physical or mechanical connections, but may include electrical connections, directly or indirectly. The terms of "up", "down", "left" or "right" and the like are only used to indicate relative position relationship, and when the absolute position of the described object changes, the relative position relationship may also change accordingly.

Grid-based administration: relying on a unified city administration and digital platform, and dividing a city administration region into unit grids according to certain standards. By strengthening inspection of components and events of the unit grids, a supervision-handling separated form is established.

An inventor of the present disclosure notices in research that, the current public event administrating system tends to extensive administration, and efficiency of data collection and screening of the current system is relatively low.

At least one embodiment of the present disclosure provides a public event administrating system. The public event involves a plurality of individuals and the provided administrating system includes a data collecting module, a data processing module, a medical resource scheduling module, and a grid administrating module. The data collecting module is configured to acquire initial data about the public event from a plurality of data sources. The data processing module is configured to process the initial data to acquire processed data. The medical resource scheduling module is configured to receive an individual service request, and allocate currently available medical resources to an individual requesting service at least according to the individual service request. And, the grid administrating module is configured to divide a geographic region managed by the administrating system into a plurality of grids, and assign a plurality of grid administrators to the plurality of grids to respectively administrate individuals in the plurality of grids. For example, the public event administrating system is conducive to the implementation of refined management.

It should be noted that, for ease of description, the public event administrating system provided by at least one embodiment of the present disclosure is exemplarily described by taking the public event as an infectious disease epidemic (e.g., COVID-19 epidemic) event which is a public health event. However, at least one embodiment of the present disclosure is not limited thereto. For example, the public event administrating system may also be configured to administrate mass disease events of unknown causes or other public events.

Hereinafter, non-limitative description of the public event administrating system provided by the embodiments of the present disclosure is provided through several examples or embodiments. As described below, different features in these specific examples or embodiments may be combined with each other without conflict, so as to obtain new examples or embodiments, and these new examples or embodiments also fall within the protection scope of the present disclosure.

FIG. 1 is an exemplary block diagram of a public event administrating system provided by at least one embodiment of the present disclosure. As shown in FIG. 1, the public event administrating system includes: a data collecting module, a data processing module, a medical resource scheduling module, and a grid administrating module.

For example, the data collecting module is configured to collect initial data about the public event from a plurality of data sources. For example, the initial data about the public event includes at least one of basic data, physical condition data, mobility data, or contact data of the plurality of individuals involved in the public event.

For example, the initial data about the public event includes the basic data, the physical condition data, the mobility data, and the contact data of the plurality of individuals involved in the public event. For example, by making the initial data about the public event include the basic data, the physical condition data, the mobility data, and the contact data of the plurality of individuals involved in the public event, a plurality of types of data (e.g., multi-dimensional data) on the plurality of individuals involved in the public event may be acquired, such that the public event may be analyzed from a plurality of aspects, making a decision maker to better understand the current situation and development trend of the public event, and further allowing the decision maker to better formulate administration strategies and schedule available resources.

For example, the basic data includes at least one (e.g., all) of address, age, gender, or identity number of an individual.

For example, the physical condition data includes at least one (e.g., all) of clinical symptom data, physical sign data, or diagnosis result data. For example, the clinical symptom data is used to indicate whether the individual has clinical symptoms of a patient suffering from an infectious disease. For example, in a case where the above-described infectious disease is COVID-19, the clinical symptoms include: fever, cough, nasal congestion, runny nose, dyspnea, diarrhea and sore throat, etc. Correspondingly, the clinical symptom data is used to indicate whether the patient has fever, cough, nasal congestion, runny nose, dyspnea, diarrhea and sore throat, etc. For example, clinical symptom data (1; 1; 1; 0; 1; 0; 0) may indicate that the patient has fever, cough, nasal congestion, and dyspnea, and does not have a runny nose, diarrhea and sore throat. For example, the physical sign data includes at least one of body temperature or blood oxygen of an individual.

For example, the mobility data includes travel history data. In one example, the travel history data is used to indicate whether an individual has a travel history in a predetermined geographic region within a predetermined period of time (e.g., within 14 days). For example, the predetermined geographic region may be at least one of a city with high incidence of infectious diseases, a floor on which a company has a cluster epidemic, or a region where animals that may carry pathogens are located. For example, the region where animals that may carry pathogens includes at least one of a slaughterhouse, a live poultry trading market, or a wildlife habitat. In another example, the travel history data includes activity trajectories of the individual. For example, the activity trajectories of the individual include cities where the individual has traveled, means of transportation, addresses where the individual has stayed, etc.

For example, the contact data includes at least one of data on whether the individual is in contact with an individual having an abnormal physical condition or data on whether the individual is in contact with an individual having a travel history in a predetermined geographic region (e.g., an epidemic region). For example, the individual having the abnormal physical condition refers to an individual who is likely to suffer from an infectious disease. For example, in a case where an individual comes into contact (e.g., close contact) with an individual having an abnormal physical condition or an individual having a travel history in a predetermined geographic region, the individual is at risk of contracting an infectious disease.

For example, the individual having the abnormal physical condition belongs to at least one of an individual having abnormal clinical symptom data, an individual having abnormal physical sign data, or an individual having an abnormal diagnosis result. For example, the individual having abnormal clinical symptom data refers to an individual having clinical symptoms as exhibited by a patient suffering from an infectious disease. For example, with respect to COVID-19, an individual having fever and dyspnea may be identified as an individual having abnormal clinical symptom data. For example, the individual having abnormal physical sign data indicates that the physical sign data of the individual is located in a data interval where the physical sign data of a patient suffering from an infectious disease is located. For example, with respect to COVID-19, an individual having a body temperature higher than 37.5 Celsius degrees may be identified as the individual having abnormal physical sign data. For example, the individual having the abnormal diagnosis result refers to an individual who has been confirmed as suffering from an infectious disease and an individual who has been confirmed as being suspected of having an infectious disease. In one example, the individual having the abnormal physical condition includes only an individual having an abnormal diagnosis result, that is, an individual is identified as the individual having the abnormal physical condition only in a case where the diagnosis result of the individual is abnormal. In this case, the number of individuals to be concerned may be reduced. In another example, the individual having the abnormal physical condition belongs to any one of an individual having abnormal clinical symptom data, an individual having abnormal physical sign data, and an individual having an abnormal diagnosis result, that is, in the case where any one of clinical symptom data, physical sign data, and diagnosis result of the individual is abnormal, the individual is identified as the individual having the abnormal physical condition. In this case, a risk of spreading infectious diseases may be reduced as much as possible.

For example, the public event administrating system further includes an individual information declaring module. For example, the individual information declaring module is configured to allow an accessing individual to declare individual data. For example, the individual data includes at least one of the basic data, the physical condition data, the mobility data, or the contact data. For example, an individual may declare (that is, upload) information for a specified number of times within specified time. For example, an individual may declare twice a day. For example, the data collecting module is configured to acquire the individual data from the individual information declaring module as at least portion of the initial data about the public event.

For example, the administrating system further includes an individual service module used in an individual terminal. For example, the individual service module is configured to communicate with the individual information declaring module to allow the individual information declaring module to collect the individual data, so that the data collecting module may acquire the individual data declared by the individual from the individual information declaring module.

For example, the individual service module may be implemented as local or front end. For example, the above-described local end or front end may be at least one of a network end, a mobile end, or a desktop end. For example, the mobile end may be one of an APP and an applet. For example, the applet may be a WeChat applet, an Alipay applet, or other applicable applets.

Figure 2:
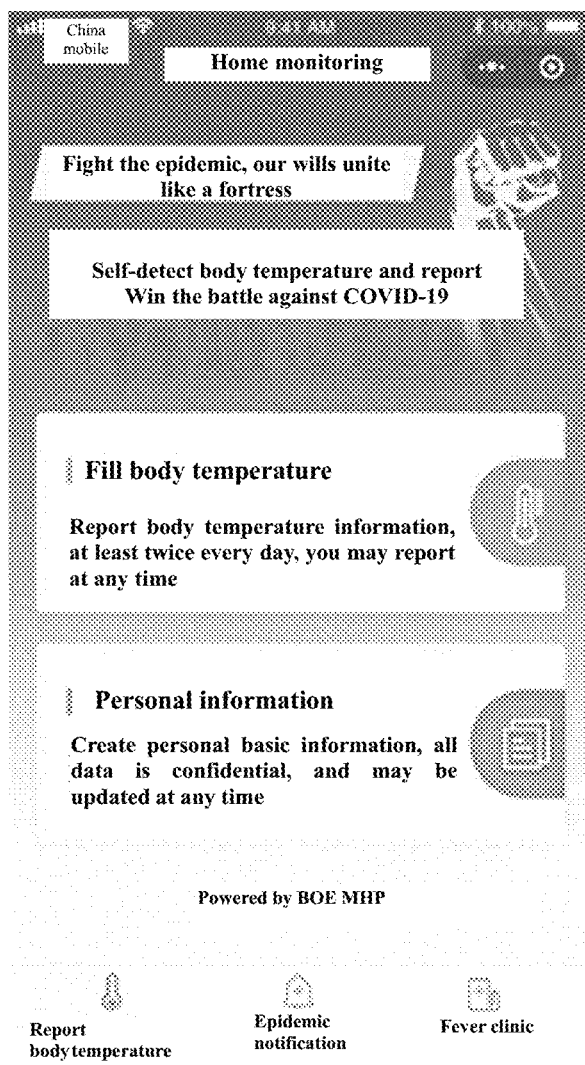
FIG. 2 is a schematic diagram of an individual service module provided by at least one embodiment of the present disclosure.
Figure 3:
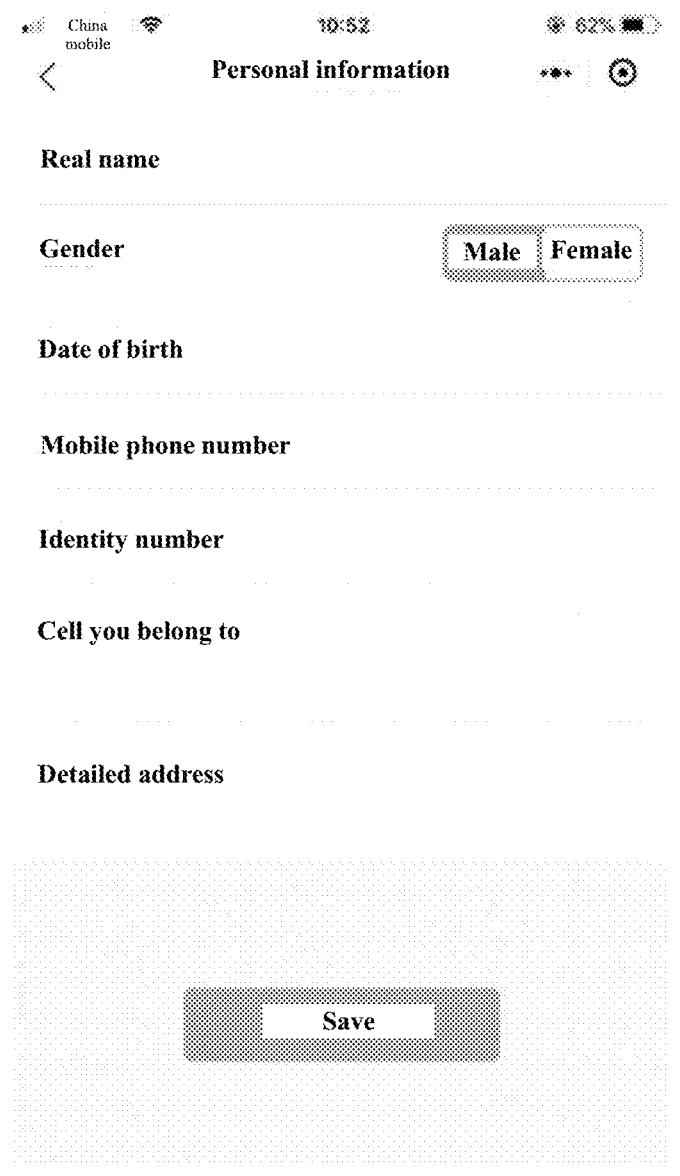

FIG. 2 is a schematic diagram of an individual service module provided by at least one embodiment of the present disclosure; FIG. 3 is a schematic diagram of an individual data collecting interface of an individual service module provided by at least one embodiment of the present disclosure; and FIG. 4 is a schematic diagram of another individual data collecting interface of an individual service module provided by at least one embodiment of the present disclosure.

For example, as shown in FIG. 2, an individual may declare basic data (i.e., personal information) and physical condition data (i.e., body temperature) of an individual via the individual service module. It should be noted that, the individual service module shown in FIG. 2 is exemplarily described by taking the administrating system as a COVID-19 administrating system. Since fever is one of main clinical manifestations of COVID-19, and body temperature is one of physical indicators of COVID-19, the individual may declare body temperature via the individual service module shown in FIG. 2, but the embodiments of the present disclosure are not limited thereto.

For example, as shown in FIG. 3, the personal information (i.e., the basic data of the individual) declared by the individual via the individual service module includes real name, gender, date of birth, mobile phone number, identity number, detailed address, and cell to which he/she belongs.

Figure 4:
FIG. 4 is a schematic diagram of another individual data collecting interface of an individual service module provided by at least one embodiment of the present disclosure.

For example, as shown in FIG. 4, an individual may also declare clinical symptom data (e.g., whether he/she has cough and other symptoms), travel history data, and contact data via the individual service module. In this case, dimensions (or types) of the individual data acquired by the data collecting module are added, so that more individuals infected with the above-described infectious disease can be screened out, to reduce the risk of spreading the infectious disease as much as possible.

For example, as shown in FIG. 4, mobility data that an individual may declare via the individual service module includes travel history data (e.g., whether he/she has been to Wuhan). For example, as shown in FIG. 4, the contact data that an individual may declare via the individual service module includes data on whether he/she has been in contact with an individual having a travel history in a predetermined geographic region (e.g., Wuhan). For example, as shown in FIG. 4, the individual service module may display historical data of body temperatures declared by the individual, so that the individual may better understand changes in his/her body temperature.

For example, the individual service module is further configured to communicate with the grid administrating module to allow the individual service module to communicate with a grid administrator of a grid to which it belongs.

For example, the data collecting module is further configured to acquire data from at least one of an online hospital admission data source, an offline hospital admission data source, an emergency rescue platform data source, a physical sign monitoring device data source, or other data sources. The acquired data may be served as at least portion of the initial data about the public event. For example, the other data sources include an epidemic prevention and control headquarter data source.

For example, by further configuring the data collecting module to acquire data from at least one of the online hospital admission data source, the offline hospital admission data source, the emergency rescue platform data source, the physical sign monitoring device data source, or the other data sources, distributed data collection can be achieved, therefore, the types of data collected by the data collecting module can be increased, and reliability of the data acquired by the data collecting module (e.g., by mutual verification with data from multiple data sources) can be improved.

For example, the data collecting module is configured to acquire data from the individual information declaring module, the online hospital admission data source, the offline hospital admission data source, the emergency rescue platform data source, the physical sign monitoring device data source, and the other data sources. In this cases, types and reliability of the data collected by the data collecting module can be further increased.

For example, the data collecting module is further configured to acquire the data of individuals seeking diagnosis in the above-described offline hospitals from the offline hospital admission data source as at least a portion of the initial data about the public event. For example, the offline hospital admission data source communicates with an offline hospital located in a geographic region managed by the administrating system to acquire at least one type of data (e.g., all types of data) of basic data, clinical symptom data, or diagnosis result data of the individual seeking diagnosis from the offline hospital located in the geographic region managed by the administrating system. For example, the above-described offline hospital may be all offline hospitals (e.g., offline hospital fever clinics) that may treat and admit the above-described infectious disease located in the geographic region managed by the administrating system. For example, by configuring the data collecting module to acquire data (e.g., basic data, clinical symptom data, and diagnosis result data) of the individual seeking diagnosis in the offline hospital from the offline hospital admission data source, professionalism of the initial data about the public event may be improved. For example, at least one of basic data, clinical symptom data, or diagnosis result data of the individual seeking diagnosis in the offline hospital located in the geographic region managed by the administrating system may exist in a form of electronic forms.

Figure 5A:
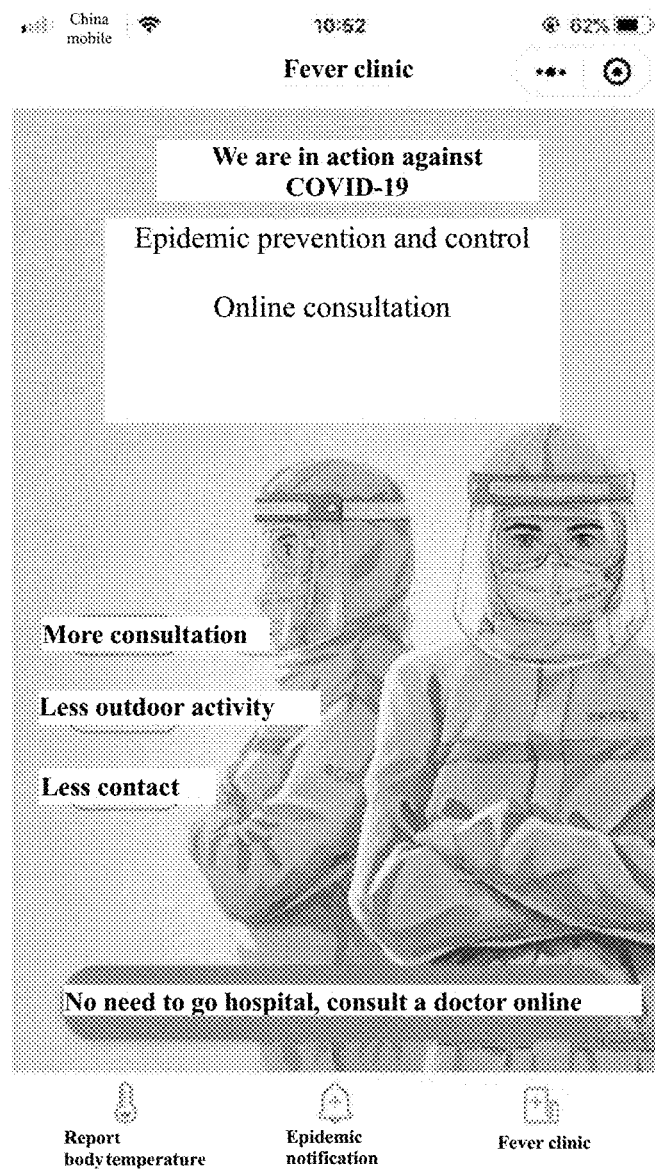
FIG. 5A is a schematic diagram of an online hospital module provided by at least one embodiment of the present disclosure.

For example, the administrating system further includes an online hospital module (e.g., an online fever clinic module). For example, the online hospital module may be implemented as a local end or a front end. For example, the above-described local end or front end may be at least one of a network end, a mobile end, or a desktop end. For example, the mobile end may be one of an APP and an applet. For example, the applet may be a WeChat applet, an Alipay applet, or other applicable applets. FIG. 5A is a schematic diagram of an online hospital module provided by at least one embodiment of the present disclosure.

For example, the above-described online hospital fever clinic module may be an online video fever clinic. For example, an individual having a fever symptom may perform real-time online video consultation with an online fever clinic doctor (e.g., a professional doctor) via the online video fever clinic, which, thus, can improve effects on consultation, diagnosis and treatment (e.g., supplied with consultation, diagnosis and treatment serves equivalent to those of an offline fever clinic). For example, since an individual having a fever symptom may perform online video consultation in his/her place of residence (e.g., at home) without traveling between the place of residence and the hospital, a risk of cross-infection is reduced (e.g., eliminated). For example, an online hospital (online video fever clinic) may be established by an offline hospital located in a geographic region managed by the administrating system. For example, online hospitals (online video fever clinics) established by different offline hospitals located in the geographic region managed by the administrating system have a unified access, thus, diagnosis and treatment resources provided by the online hospitals can be better allocated.

For example, the online hospital module (online video fever clinic module) may acquire basic information such as real location and real phone number of an individual seeking diagnosis. Thus, in this case, a decision maker (e.g., epidemic prevention and control headquarter) can comprehensively acknowledge (e.g., in real time) a situation of fever patients in the geographic region managed by the administrating system, such that, medical resources can be better allocated with the provided data support for decision-making.

Figure 5B:
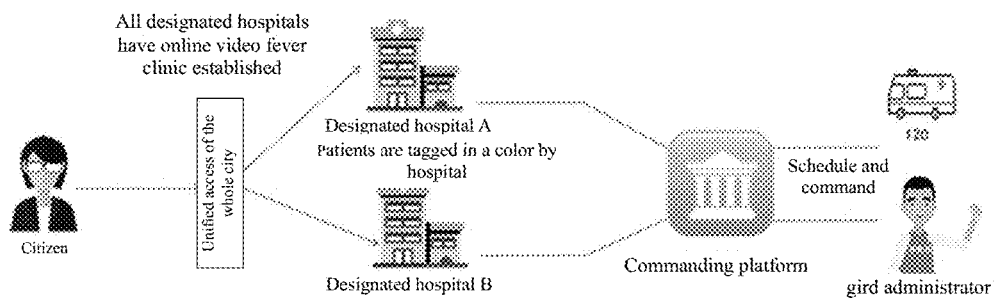
FIG. 5B is a schematic diagram of a reception scheme of an online video fever clinic provided by at least one embodiment of the present disclosure.

FIG. 5B is a schematic diagram of a reception scheme of an online video fever clinic provided by at least one embodiment of the present disclosure. As shown in FIG. 5B, a unified access for online video fever clinics may be established on an applet (e.g., a WeChat applet) or an APP; and citizens may be treated by professional doctors through the applet or the APP. For example, an admitting doctor may belong to a designated hospital for fever located in a place positioned by a citizen's mobile phone. For example, when a citizen has a body abnormality (e.g., has a temperature higher than 39 Celsius degrees), an epidemic prevention and control headquarter may dispatch and command grid administrators and ambulances according to an online admission situation of designated hospitals for fever in respective regions.

For example, the data collecting module is further configured to acquire data of an individual seeking diagnosis in an online hospital (e.g., an online hospital module) from an online hospital admission data source, as at least a portion of the initial data about the public event. For example, the online hospital admission data source communicates with an online hospital (e.g., an online hospital module) that serves the individuals in the geographic region managed by the administrating system, so as to acquire at least one type of data (e.g., all types of data) of basic data, clinical symptom data, or diagnosis result data of the individual seeking diagnosis in the above-described online hospital (e.g., online hospital module) from the above-described online hospital (e.g., online hospital module) that provides services for the individuals in the geographic region managed by the administrating system. For example, the above-described online hospital (e.g., online hospital module) may include all online hospitals (e.g., online hospital fever clinics) serving the individuals in the geographic region managed by the administrating system that may treat the above-described infectious diseases. For example, by configuring the data collecting module to acquire data (e.g., basic data, clinical symptom data, and diagnosis result data) of the individual seeking diagnosis in the online hospital from the online hospital admission data source, professionalism of the initial data about the public event can be improved.

For example, the data collecting module is further configured to acquire physical sign data of an individual from the physical sign monitoring device data source, as at least a portion of the initial data about the public event. For example, by further configuring the data collecting module to acquire physical sign data of the individual from the physical sign monitoring device data source, authenticity or accuracy of the individual's physical sign data acquired by the data collecting module can be improved. For example, misoperations in manually reading or filling in physical sign data may be avoided.

For example, the physical sign monitoring device data source communicates with a plurality of physical sign monitoring devices. For example, the plurality of physical sign monitoring devices include at least one of a body temperature detecting device provided in a public place, an instrument for monitoring patients provided in a hospital, or a wearable monitoring terminal. For example, the body temperature detecting device provided in a public place includes a forehead thermometer, a body temperature detecting door, or other applicable body temperature detecting devices. For example, the instrument for monitoring patients provided in a hospital may be used to monitor the physical signs of patients. For example, the instrument for monitoring patients provided in a hospital may include oximeters, physical sign monitors, etc. For example, the wearable monitoring terminal may monitor physical sign information (e.g., at least one of body temperature or blood oxygen) of a user wearing the wearable monitoring terminal. For example, the wearable monitoring terminal may include a smart watch, a blood oxygen clip or other applicable monitoring terminals. For example, the physical sign monitoring device may also be a physical sign monitoring device that may automatically upload a physical sign monitoring result to the physical sign monitoring device data source.

In an example, the physical sign monitoring device may only upload abnormal physical sign data to the physical sign monitoring device data source, which, thus, may reduce a communication volume between the physical sign monitoring device data source and the physical sign monitoring device. For example, in a case where a body temperature detected by the body temperature detecting device is higher than 37.5 Celsius degrees, the body temperature detecting device uploads the above-described body temperature and information of the individual corresponding to the body temperature to the physical sign monitoring device data source. In another example, the physical sign monitoring device may upload the physical sign data detected in predetermined time (every morning and evening) to the physical sign monitoring device data source, so that the individual's physical sign change trend may be tracked.

For example, the data collecting module is further configured to acquire individual physical sign data from the epidemic prevention and control headquarter data source, as at least a portion of the initial data about the public event. For example, the epidemic prevention and control headquarter data source communicates with the epidemic prevention and control headquarter.

For example, the initial data about the public event acquired by the data collecting module may be stored in a memory or a database. For example, the memory may include at least one of a volatile memory or a non-volatile memory. For example, the memory may include a Read-Only Memory (ROM), a hard disk, a flash memory, and the like. For example, the above-described memory or database may be interconnected or communicate with the data collecting module via a network or other technologies (e.g., Bluetooth communication, infrared communication, etc.), so that the data collecting module may store the initial data about the public event in the above-described memory or database.

For example, the above-described network may be a single network, or a combination of at least two different networks. For example, the network may include, but is not limited to, one or a combination of several of a local area network, a wide area network, a public network, a private network, the Internet, and a mobile communication network.

For example, the above-described memory or database may be interconnected or communicate with the data processing module via a network or other technologies (e.g., Bluetooth communication, infrared communication, etc.), so that the data processing module may read at least a portion of the above-described initial data about the public event from the above-described memory or database.

For example, the data processing module is configured to process the initial data about the public event to obtain processed data. For example, the processed data includes at least one type of following data: a list of abnormal individuals respectively belonging to the plurality of grids; a list of individuals respectively belonging to the plurality of grids who have not declared individual data within predetermined time; a list of individuals respectively belonging to the plurality of grids who have declared individual data within predetermined time; a list of newly added individuals respectively belonging to each grid; a statistical result of current physical conditions of the plurality of individuals involved in the public event; change trends of focused individuals among the plurality of individuals involved in the public event; or a statistical result of regional distribution of the focused individuals among the plurality of individuals involved in the public event.

For example, the abnormal individual belongs to at least one of an individual having an abnormal physical condition, an individual having a travel history in a predetermined geographic region, an individual having been in contact with an individual having an abnormal physical condition, or an individual having been in contact with an individual having a travel history in a predetermined geographic region. For example, the individual having an abnormal physical condition belongs to at least one of an individual having abnormal clinical symptom data, an individual having abnormal physical sign data, or an individual having an abnormal diagnosis result. For example, the data processing module may acquire a list of abnormal individuals in the plurality of grids by comparing relevant data of the plurality of individuals in the plurality of grids with preset data. For example, the data processing module may acquire a list of individuals in the plurality of grids having abnormal body temperatures by comparing the body temperatures of the plurality of individuals in the plurality of grids with a preset body temperature threshold (e.g., 37.5 Celsius degrees).

For example, the data processing module may acquire the list of individuals who have not declared individual data within predetermined time in the plurality of grids by comparing the list of the plurality of individuals in the plurality of grids with the list of individuals who have declared individual data within predetermined time. For example, the data processing module may acquire the list of individuals in the plurality of grids who have not declared individual data within a current day by comparing the list of the plurality of individuals in the plurality of grids and the list of individuals who have declared individual data within the current day.

For example, a newly added individual in each grid may be an individual having moved into the grid from another grid. For example, the data processing module may acquire a list of newly added individuals respectively belonging to each grid by searching for individuals whose addresses have changed.

For example, the statistical result of current physical conditions of the plurality of individuals involved in the public event include at least one of a statistical result of current physical sign data of the plurality of individuals involved in the public event or a statistical result of current clinical symptom data of the plurality of individuals involved in the public event. For example, the focused individuals belong to at least one of confirmed individuals, suspected individuals, cured individuals, dead individuals, individuals in close contact with confirmed individuals, individuals under medical observation among the individuals in close contact with confirmed individuals, or individuals released from medical observation among the individuals in close contact with confirmed individuals.

For example, the grid administrating module is configured to divide a geographic region managed by the administrating system into the plurality of grids, and assign the plurality of grid administrators to the plurality of grids to respectively administrate individuals in the plurality of grids; which, thus, refined administration can be achieved.

In one example, the geographic region managed by the administrating system may be a physical geographic region. For example, if the geographic region managed by the administrating system is a city; and the city may be divided into the plurality of grids (e.g., each cell being one grid).

In another example, the geographic region managed by the administrating system may be a virtual geographic region; and in this case, the plurality of individuals in the grid may be scattered in different physical geographic regions. For example, the geographic region managed by the administrating system is a school, and the school may be divided into the plurality of grids (e.g., each class being one grid). For another example, the geographic region managed by the administrating system is an industry, and the industry is divided into the plurality of grids (e.g., each unit of the industry being one grid).

For example, the grid administrating module includes a grid dividing sub-module and a grid administrator sub-module. For example, the grid dividing sub-module is configured to divide the region managed by the administrating system into the plurality of grids. For example, the grid administrator sub-module is configured to respectively establish communications with the plurality of grid administrators.

For example, the administrating system further includes a grid administrator terminal module used in a terminal held by each of the plurality of grid administrators. For example, the grid administrator terminal module may be implemented as a local end or a front end. For example, the above-described local end or front end may be at least one of a network end, a mobile end, or a desktop end. For example, the mobile end may be one of an APP and an applet. For example, the applet may be a WeChat applet, an Alipay applet, or other applicable applets.

Figure 6:
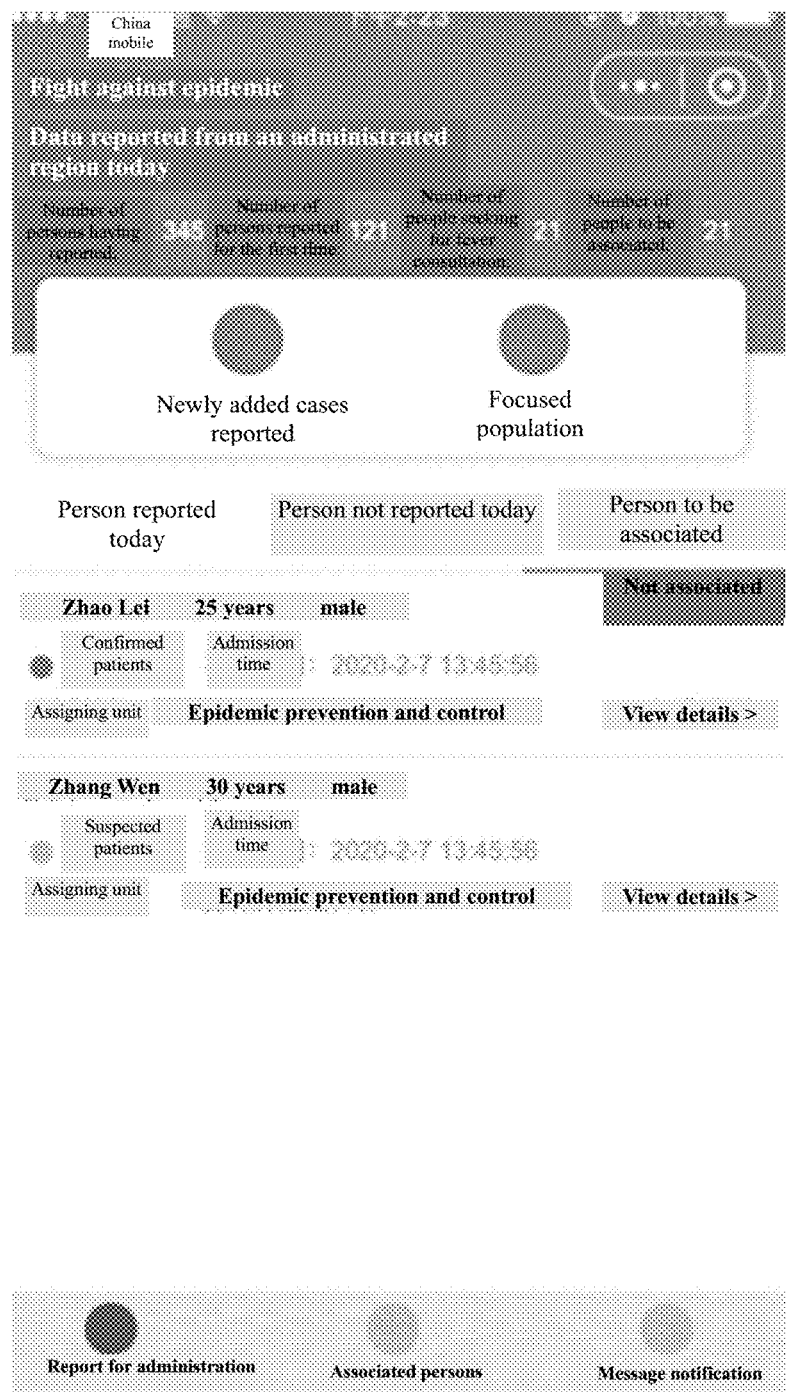
FIG. 6 is a schematic diagram of a grid administrator terminal module provided by at least one embodiment of the present disclosure.

FIG. 6 is a schematic diagram of a grid administrator terminal module provided by at least one embodiment of the present disclosure. For example, the grid administrator terminal module is configured to communicate with the grid administrator sub-module, so that the grid administrator sub-module may respectively establish communications with the plurality of grid administrators.

For example, the grid administrator sub-module is further configured to respectively associate the plurality of individuals in the plurality of grids with the plurality of grids and to respectively associate the plurality of individuals in the plurality of grids with the plurality of grid administrators (or grid administrator terminal modules), so that the plurality of grid administrators may respectively administrate the plurality of individuals in the plurality of grids.

It should be noted that, since the grid administrator may acquire, through the grid administrator terminal module, received data by the grid administrator terminal module, in the following description, the grid administrator receiving relevant data indicates that the grid administrator terminal module receives the relevant data, and then the grid administrator acquires, through the grid administrator terminal module, the relevant data received by the grid administrator terminal module.

For example, the administrator sub-module may grant corresponding permissions (e.g., data acquisition permission, and data read permission in the memory or the database) to the plurality of grid administrator terminal modules, so that the plurality of grid administrators (or grid administrator terminal modules) are respectively associated with the plurality of individuals in the plurality of grids.

For example, the grid administrating module (e.g., the grid administrator sub-module) is further configured to acquire the initial data about the public event from the data collecting module. Each grid administrator terminal module has permissions to receive, from the grid administrating module (e.g., the grid administrator sub-module), relevant data of the plurality of individuals in the grid corresponding to the grid administrator terminal module that is supplied by the grid administrating module (e.g., the grid administrator sub-module), so that the grid administrator terminal module is associated with the plurality of individuals located in the grid corresponding to the grid administrator terminal module, and further the grid administrator using the grid administrator terminal module may administrate (e.g., perform targeted and refined administration on) the plurality of individuals in the corresponding grid based on the above-described relevant data of the plurality of individuals.

For example, the grid administrating module (e.g., the grid administrator sub-module) may acquire, from the data collecting module, individual data declared by an individual (e.g., basic data, physical condition data, mobility data, and contact data) acquired by the data collecting module from individual information declaring module, and respectively supply the above-described individual data to a corresponding grid administrator (or grid administrator terminal module). For example, the grid administrating module (e.g., the grid administrator sub-module) may also acquire, from the data collecting module, basic data, clinical symptom data, and diagnosis result data of an individual seeking diagnosis in an online hospital and an offline hospital acquired by the data collecting module from the online hospital admission data source and the offline hospital admission data source, and respectively supply the above-described basic data, clinical symptom data, and diagnosis result data of the individual to a corresponding grid administrator (or grid administrator terminal module). For example, the grid administrating module (e.g., the grid administrator sub-module) may also acquire, from the data collecting module, the physical sign data of the individual acquired by the data collecting module from the physical sign monitoring device data source, and respectively supply the physical sign data of the above-described individual to a corresponding grid administrator (or grid administrator terminal module).

For example, the processed data includes a list of abnormal individuals respectively belonging to the plurality of grids. The grid administrating module (e.g., the grid administrator sub-module) is configured to acquire, from the data processing module, the list of abnormal individuals respectively belonging to the plurality of grids, and respectively supply the list of abnormal individuals respectively belonging to the plurality of grids to the plurality of grid administrators.

For example, the grid administrating module (e.g., the grid administrator sub-module) is configured to respectively supply a list of abnormal individuals belonging to each grid to a grid administrator (or a grid administrator terminal module) associated with the grid. For example, the grid administrator may click "Focused population" in the grid administrator terminal module shown in FIG. 6 to acquire the list of abnormal individuals in the grid administrated by the grid administrator that is received by the grid administrator terminal module.

For example, by configuring the grid administrating module (e.g., the grid administrator sub-module) to respectively supply the list of abnormal individuals belonging to each grid to the grid administrator (or the grid administrator terminal module) associated with the grid, the grid administrator may screen individuals in the list of abnormal individuals without screening normal individuals in the grid, which, thus, screening efficiency can be improved, workload of the grid administrator can be reduced, and missed checked (i.e., failure of completely screening all individuals in the grid administrated thereby) due to excessive workload can be avoided. For example, screening individuals in the list of abnormal individuals includes reviewing at least one of basic data, physical condition data, mobility data, or contact data of the individuals in the list of abnormal individuals, so that the accuracy of data collected by the data collecting module can be ensured. For example, screening individuals in the list of abnormal individuals includes reviewing body temperatures of the individuals in the list of individuals having an abnormal temperature, so as to reduce false abnormalities caused by reading or filling errors.

For example, the grid administrator may communicate individuals in the list of abnormal individuals by phone or through the Internet, and perform information collection remotely, which, thus, screening and reviewing of the at least one of basic data, physical condition data, mobility data, or contact data of individuals in the list of abnormal individuals can be performed while reducing the risk of infection of such as the administrator and improving work efficiency can be achieved.

For example, by configuring the grid administrating module (e.g., the grid administrator sub-module) to respectively supply the list of abnormal individuals belonging to each grid to the grid administrator (or the grid administrator terminal module) associated with the grid, the grid administrator may devote more energy in serving the individuals in the list of abnormal individuals (e.g., making the individuals on the list of abnormal individuals get timely treatment when their physical conditions deteriorate).

For example, the processed data includes a list of individuals respectively belonging to the plurality of grids who have not declared individual data within predetermined time. For example, the grid administrating module (e.g., the grid administrator sub-module) is configured to acquire, from the data processing module, the list of individuals respectively belonging to the plurality of grids who have not declared individual data within predetermined time, and respectively supply the list of individuals respectively belonging to the plurality of grids who have not declared individual data within predetermined time to the plurality of grid administrators (or grid administrator terminal modules). For example, the grid administrator may click "Persons not reported today" in the grid administrator terminal module shown in FIG. 6 to acquire the list of individuals belonging to the grid administrated by the grid administrator who have not declared individual data within the current day that is received by the grid administrator terminal module. For example, the grid administrator may urge (e.g., by telephone or online supervision) the individuals who have not declared individual data within the current day to declare individual data one by one based on the list of individuals who have not declared individual data within the current day, so that data collected by the data collecting module is more complete.

In some examples, the grid administrating module (e.g., the grid administrator sub-module) is further configured to acquire, from the data processing module, the list of individuals respectively belonging to the plurality of grids who have declared individual data within predetermined time, and respectively supply the list of individuals respectively belonging to the plurality of grids who have declared individual data within predetermined time to the plurality of grid administrators (or grid administrator terminal modules). For example, the grid administrator may click "Persons reported today" in the grid administrator terminal module shown in FIG. 6 to acquire the list of individuals belonging to the grid administrated by the grid administrator who have declared individual data within the current day that is received by the grid administrator terminal module.

For example, the grid administrator sub-module is further configured to respectively assign screening tasks to the plurality of grid administrators (or grid administrator terminal modules), and is configured to acquire feedback information on the assigned screening tasks from the plurality of grid administrators. For example, the grid administrator may click "Person required to be associated" in the grid administrator terminal module shown in FIG. 6 to acquire a screening task (i.e., screening "persons required to be associated") that is received by the grid administrator terminal module. For example, after completing the screening task, the grid administrator may upload a screening result via the grid administrator terminal module, so that the grid administrator sub-module may acquire, from the grid administrator, feedback information on the assigned screening task. For example, the above-described "persons required to be associated" may be an individual (e.g., an individual isolated at home) having normal physical condition data, but having been in contact (e.g., close contact) with an individual having been diagnosed to have an infectious disease or suspected of having an infectious disease.

For example, the grid administrator terminal module is further configured to allow each of the plurality of grid administrators to tag a specific individual in the grid administrated thereby and upload tag data. For example, the grid administrator may tag (e.g., with a color tag or a symbol tag), via the administrator terminal module, a plurality of individuals in the grid administrated by the grid administrator based on at least one of physical condition data, mobility data, or contact data of the plurality of individuals in the grid administrated by the grid administrator. For example, the grid administrator may tag an individual diagnosed to have an infectious disease in the grid administrated by the grid administrator as red, and tag an individual suspected of having an infectious disease in the grid administrated by the grid administrator as yellow.

For example, the processed data includes the list of newly added individuals respectively belonging to the plurality of grids. The grid administrating module (e.g., the grid administrator sub-module) is configured to acquire, from the data processing module, the list of newly added individuals respectively belonging to the plurality of grids, and respectively supply the list of newly added individuals respectively belonging to the plurality of grids to the plurality of grid administrators.

For example, the grid administrating module (e.g., the grid administrator sub-module) is configured to respectively supply the list of newly added individuals belonging to each grid to the grid administrator (or the grid administrator terminal module) associated with the grid. For example, the grid administrator may click "Report of newly added cases" in the grid administrator terminal module shown in FIG. 6 to acquire the list of newly added individuals in the grid administrated by the grid administrator that is received by the grid administrator terminal module. For example, by configuring the grid administrating module (e.g., the grid administrator sub-module) to respectively supply the list of newly added individuals belonging to each grid to the grid administrator (or the grid administrator terminal module) associated with the grid, the grid administrator may devote more energy to the newly added individuals in the grid administrated by the grid administrator (e.g., in acknowledging relevant situation of the newly added individuals timely).

For example, the grid administrator terminal module may communicate with the individual service module via the grid administrating module (e.g., the grid administrator sub-module), so that the individual may communicate with the grid administrator of the grid to which he/she belongs via the corresponding individual service module and the corresponding grid administrator terminal module. For example, the grid administrator may click "Message notification" in the grid administrator terminal module shown in FIG. 6 to acquire a message sent by an individual in the grid administrated thereby.

Figure 7:
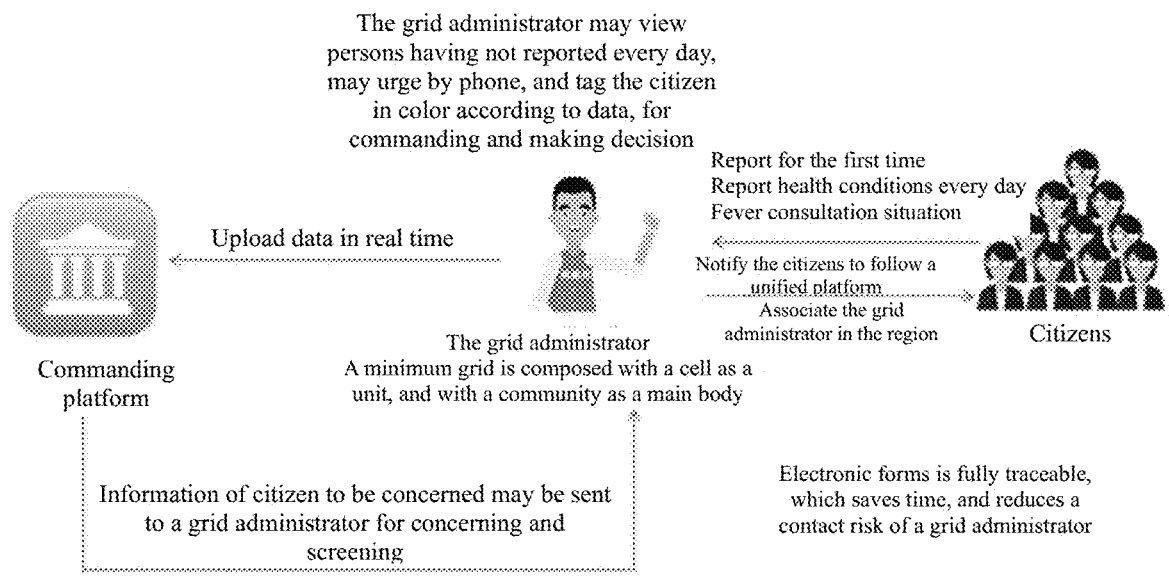
FIG. 7 is a scheme flow chart for screening fever population and administrating population isolated at home by a grid administrator provided by at least one embodiment of the present disclosure.

FIG. 7 is a scheme flow chart screening fever population and administrating population isolated at home by a digitized grid administrator (grid-based administration) provided by at least one embodiment of the present disclosure. As shown in FIG. 7, in the grid-based administration scheme, each cell of a city administrated thereby is taken as a grid, and each grid is allocated with a grid administrator (e.g., a community doctor); the grid administrator of each grid is responsible for administrating information statistics and health situations of citizens in the grid administrated by the grid administrator. For example, the grid administrator informs the citizens to follow a unified platform (e.g., the individual information declaring module implemented as an applet); when the citizens follow the unified platform and fill in basic data (e.g., name, identity number, cell to which they belong, community, phone number, etc.), the grid administrator sub-module respectively associates the citizens (e.g., citizens' basic data) with the plurality of grids and the plurality of grid administrators (or grid administrator terminal modules) based on the cell to which they belong. For example, when a physical condition of a citizen in the grid administrated by the grid administrator is abnormal, the grid administrator may check personal information (e.g., address and phone number) of the citizen having the abnormal physical condition, and may timely contact the citizen having the abnormal physical condition. For example, the citizen needs to report body temperature, symptom and other information daily. For example, the citizen may report information such as body temperature, daily symptom and other information via an individual data collecting interface of the individual service module shown in FIG. 3 and FIG. 4. For example, the citizen may also conduct fever consultation via the online hospital module shown in FIG. 5A. For example, the information such as body temperature and daily symptom reported through the individual data collecting interface of the individual service module and fever consultation information of citizens seeking diagnosis acquired by the online hospital module may be supplied (e.g., via the data collecting module, the administrator sub-module and the grid administrator terminal module) to the grid administrator. For example, the grid administrator can view, through the grid administrator terminal module shown in FIG. 6, citizens having not uploaded health data within a current day in the grid administrated thereby, query (e.g., query the memory or the database storing the initial data about the public events) basic information of the citizens having not uploaded health data, and urge, by telephone, those citizens having not uploaded health data to declare health data. For example, the grid administrator may tag citizens with colors based on health data uploaded by the citizens, for a decision maker (e.g., an epidemic prevention and control headquarter) to command and make decisions. For example, according to health report situations of respective grids, the decision maker sends information of citizens who need to be closely watched to the grid administrator, so as to focus and screen specific situations. For example, the scheme shown in FIG. 7 for screening fever population and administrating population isolated at home has advantages of improving screening efficiency of the grid administrator (reducing time required for screening each individual) and reducing the risk of infecting the grid administrator. For example, since the health data uploaded by the citizens and the data uploaded by the grid administrator are all electronic data (e.g., in the form of electronic forms), the scheme shown in FIG. 7 also has the advantage of data traceability.

For example, the processed data further includes at least one of a statistical result of current physical conditions of the plurality of individuals involved in the public event, a trend of changes in focused individuals among the plurality of individuals involved in the public event, or a statistical result of regional distribution of focused individuals among the plurality of individuals involved in the public event.

For example, the public event administrating system further includes a data display platform. For example, the statistical result of current physical conditions of a plurality of individuals involved in the public event, the trend of changes in focused individual among the plurality of individuals involved in the public event, and the statistical results of regional distribution of focused individuals among the plurality of individuals involved in the public event may be displayed on the data display platform, and based on the relevant processed data displayed on the data display platform, the decision maker (e.g., the epidemic prevention and control headquarter) can make decisions.

Figure 8:
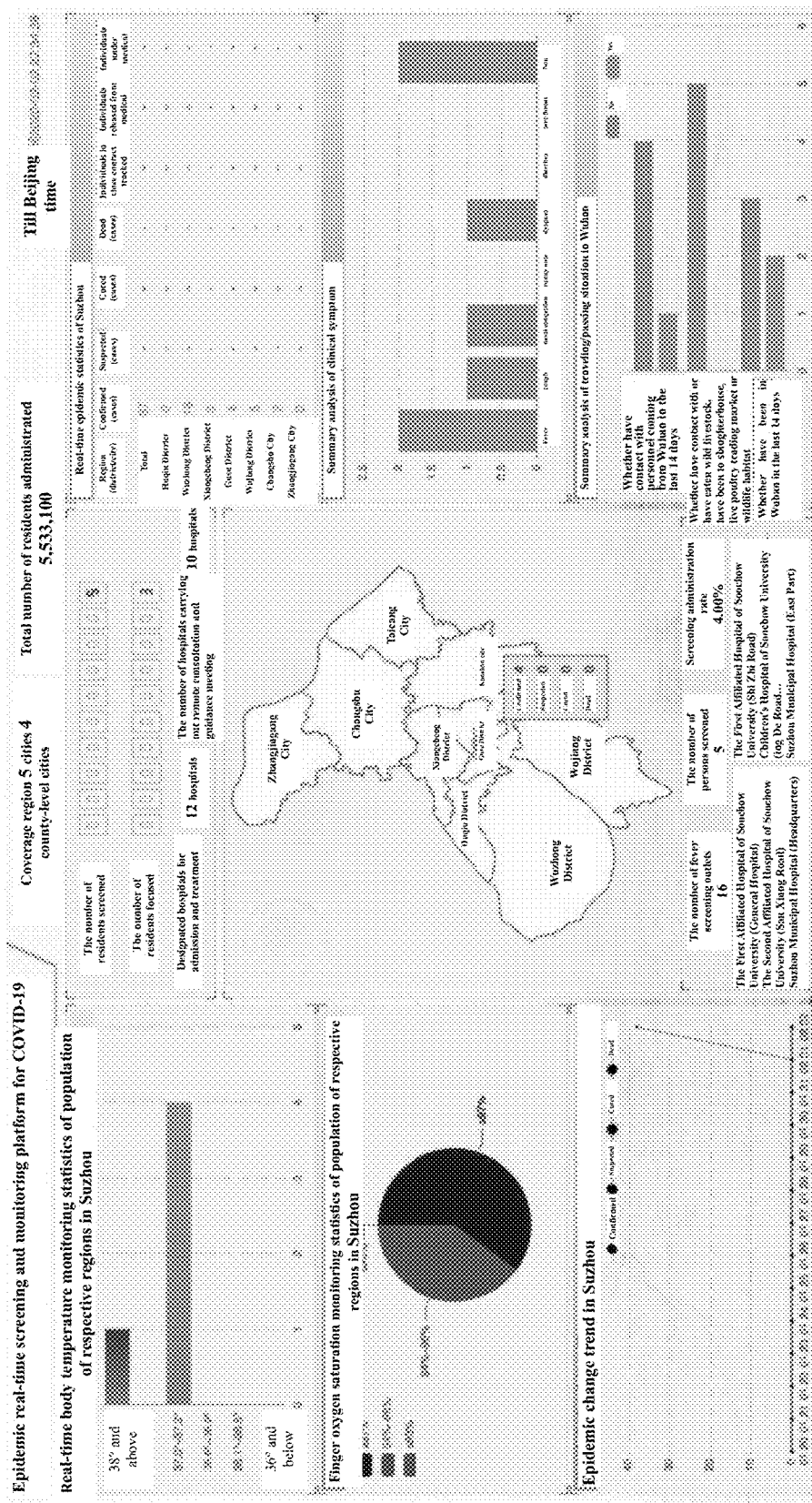
FIG. 8 is a schematic diagram of a display interface of a data display platform provided by at least one embodiment of the present disclosure.

For example, FIG. 8 is a schematic diagram of a display interface of the data display platform (e.g., a data perspective platform for fever population dynamic information) provided by at least one embodiment of the present disclosure. For example, as shown in FIG. 8, the data display platform may present a real-time epidemic situation, and present the processed data (e.g., the statistical results reported by the residents of the city) in a visual way.

For example, as shown in FIG. 8, the display interface (e.g., a screen, or a large screen) of the data display platform has three columns in a horizontal direction. A left column shows a bar chart of real-time body temperature monitoring statistics and a pie chart of finger oxygen saturation monitoring statistics of population in respective regions of the city, to facilitate the epidemic prevention and control headquarter to acknowledge (e.g., in real time) abnormal situations likely to occur. The left column also shows a city's epidemic change trend chart for reflecting an overall situation of the city's epidemic situation in real time.

For example, a middle column of FIG. 8 shows the number of screened (e.g., investigated) residents and the number of focused residents. The middle column also shows a map of the city, so that the number of confirmed, suspected, cured, and dead persons of respective regions in the city may be viewed by clicking the respective regions on the map of the city. A bottom portion of the middle column shows fever screening outlets (e.g., fever clinics) of the city and the number of screened (investigated) persons, so as to facilitate the epidemic prevention and control headquarter to acknowledge the schedulable resources of the city.

For example, a top portion of a right column of FIG. 8 shows real-time statistical results of epidemic situations in respective regions of the city. For example, the real-time statistical results of the epidemic situation include statistical results of the number of citizens having clinical symptoms (e.g., fever, cough, nasal congestion, etc.) (displayed by a bar chart). As an example, a bottom portion of the right column of FIG. 8 also shows statistical results of citizens of the city traveling to or passing through the city of Wuhan.

For example, the epidemic prevention and control headquarter may acknowledge dynamic distribution of fever population (citizens) in real time through the data displayed on the display interface (e.g., large screen) of the data display platform, and may issue a screening task to a grid administrator corresponding to a grid where a fever citizen is located, so that the grid administrator may monitor or dynamically administrate symptoms and body temperature of the fever citizen. For example, data such as clinical symptoms and body temperature of associated personnel uploaded by the grid administrator may be transmitted back to the epidemic prevention and control headquarter in real time, so that the epidemic prevention and control headquarter may timely issue information (e.g., name, address, telephone number, clinical symptoms, body temperature, etc.) of a citizen whose clinical symptoms and body temperature have abnormal changes among citizens monitored at home to an emergency rescue platform, and the emergency rescue platform may dispatch a professional ambulance for transporting the citizen whose clinical symptoms and body temperature have abnormal changes among the citizens monitored at home to hospital for treatment or transporting the citizen to a centralized isolation point for observation.

For example, the medical resource scheduling module is configured to receive an individual service request, and allocate, at least according to the individual service request, currently available medical resources to the individual requesting service.

For example, the medical resource scheduling module includes a hospital scheduling sub-module. For example, the hospital scheduling sub-module is configured to allocate an offline admitting hospital to the individual requesting service, or to establish a connection between the individual requesting service and a hospital supplying online service, based on positioning data of the individual requesting service, admission amount of the hospital, and a physical condition of the individual requesting service.

In one example, the medical resource scheduling module further includes an ambulance scheduling sub-module. The hospital scheduling sub-module is configured to allocate an offline admitting hospital to the individual requesting service; and the ambulance scheduling sub-module is configured to allocate an ambulance for the individual requesting service based on positioning data of the individual requesting service, and distribution situation of offline hospitals (e.g., addresses of offline hospitals) and currently available ambulances.

In another example, the hospital scheduling sub-module is configured to establish a connection between the individual requesting service and a hospital supplying online service. For example, the hospital scheduling sub-module is further configured to acquire (from the hospital supplying online service) diagnostic data of the individual requesting service and supply the diagnostic data of the individual requesting service to the data collecting module.

For example, the individual service module is configured to communicate with the medical resource scheduling module to send the individual service request and establish service connections.

For example, the public event administrating system further includes an information supplying module. For example, the information supplying module is configured to publish at least one of statistical results of focused individuals, protection knowledge, or rumor-refuting information. For example, the information supplying module is further configured to publish at least one of travel history information of confirmed individuals or medical resource information of a designated region.

Figure 9:
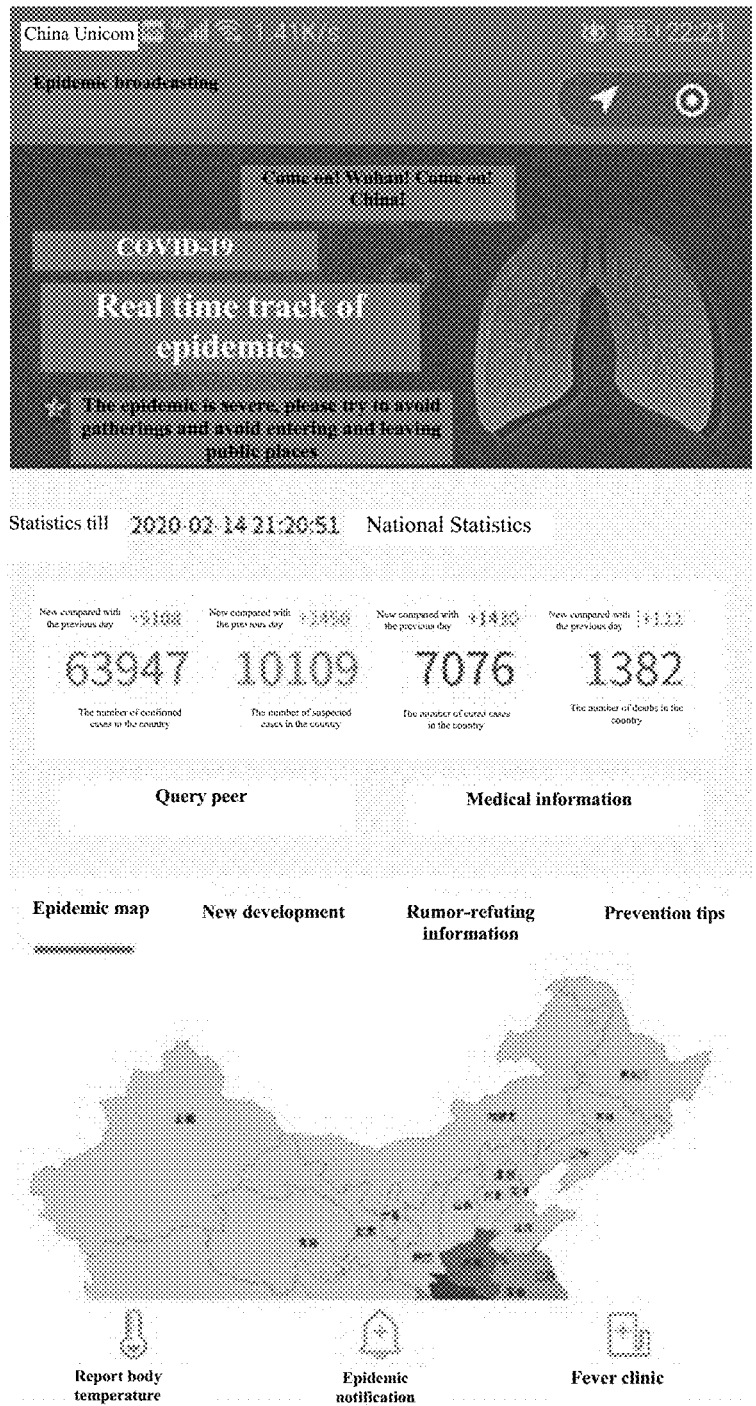
FIG. 9 is a schematic diagram of an information supplying module provided by at least one embodiment of the present disclosure.

FIG. 9 is a schematic diagram of an information supplying module provided by at least one embodiment of the present disclosure. For example, as shown in FIG. 9, the information supplying module may supply statistical results of focused individuals in a form of an epidemic map (e.g., the number of confirmed patients, suspected cases, the number of cured cases, and the number of deaths across the country). For example, by configuring the information supplying module to supply the statistical results of focused individuals (e.g., the number of confirmed patients, suspected cases, the number of cured cases, and the number of deaths across the country), timely epidemic broadcasting may be implemented, which, thus, may enhance the individuals' sense of trust and facilitate the individuals to understand the current epidemic situation at any time.

For example, as shown in FIG. 9, the information supplying module is further configured to publish the rumor-refuting information. For example, the rumor-refuting information released by the information supplying module may be acquired by clicking "Rumor-refuting information" shown in FIG. 9. For example, the function of publishing rumor-refuting information may prevent residents from panicking or suffering injuries due to incorrect or false information. For example, as shown in FIG. 9, the information supplying module is further configured to publish protection knowledge. For example, the protection knowledge released by the information supplying module may be acquired by clicking "Prevention tips" as shown in FIG. 9. For example, by further configuring the information supplying module to publish the protection knowledge, the individuals' understanding of the protection knowledge may be increased, and the individuals' infection rate may be reduced through scientific protection.

For example, the information supplying module is further configured to supply travel history information of a confirmed individual. For example, the travel history information of the confirmed individual may be acquired by query. For example, the travel history information of the confirmed individual released by the information supplying module may be acquired by clicking "Peer inquiry" shown in FIG. 9. For example, the function of inquiring peer of the confirmed patient helps individuals to inquire whether they are at risk of being infected, which is used for early discovering infected persons and reducing a rate of spreading infectiousness by the infected persons.

For example, the information supplying module is further configured to supply medical resource information in a designated region. For example, medical resource information in the designated region may be acquired by inquiry. For example, the medical resource information of the designated region released by the information supplying module may be acquired by clicking the button of "Medical information" shown in FIG. 9. For example, medical information contains information of offline fever clinics and designated hospitals. For example, when an individual clicks "Medical information" shown in FIG. 9, a medical information sub-module may automatically help the individual find available medical resources (e.g., an available admitting hospital) near the individual based on the positioning information of the individual.

For example, the information supplying module may be implemented as a local end or a front end. For example, the above-described local end or front end may be at least one of a network end, a mobile end, or a desktop end. For example, the mobile end may be one of an APP and an applet. For example, the applet may be a WeChat applet, an Alipay applet, or other applicable applets.

For example, the data collecting module, the data processing module, the medical resource scheduling module, the grid administrating module (e.g., any one of the grid dividing sub-module and the grid administrator sub-module) and the individual information declaring module may be implemented through software, firmware, and hardware, or an arbitrary combination of software, firmware, and hardware. For example, the hardware includes a Field Programmable Gate Array (FPGA), etc.

Figure 10:
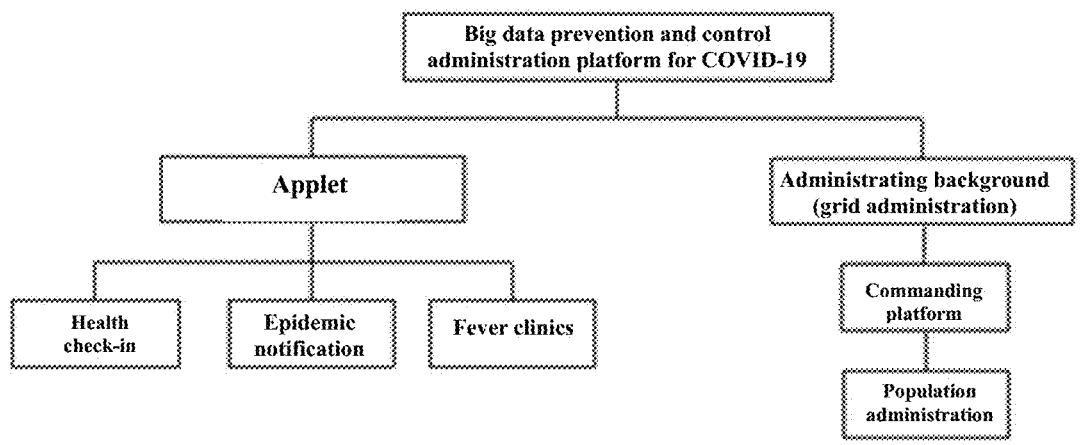
FIG. 10 is an exemplary block diagram of a big data prevention and administration platform for a Corona Virus Disease 2019 (COVID-19) according to at least one embodiment of the present disclosure.

FIG. 10 is an exemplary block diagram of a big data prevention and control administration platform for the Corona Virus Disease 2019 (COVID-19) according to at least one embodiment of the present disclosure. For example, as shown in FIG. 10, the big data prevention and control administration platform for COVID-19 can implement, through an applet, a health check-in module (e.g., corresponding to the foregoing individual service module and grid administrator terminal module), an epidemic notifying module (e.g., corresponding the foregoing information supplying module) and a fever clinic module (e.g., corresponding to the foregoing online hospital module). For example, as shown in FIG. 10, the big data prevention and control administration platform for COVID-19 further includes an administrating background platform (e.g., corresponding to the foregoing grid administrating module, the medical resource scheduling module, etc.). For example, a command platform (e.g., corresponding to the foregoing epidemic prevention and control headquarter) may administrate individuals in the geographic region managed by the big data prevention and control administration platform for COVID-19 through the grid administrating module and the medical resource scheduling module.

For example, the big data prevention and control administration platform for COVID-19 provided by at least one embodiment of the present disclosure creates a multi-level and multi-module public health emergency system, and plays an important role of an information platform in assisting epidemic resistance and improving prevention and control efficiency.

For example, the public event administrating system and the big data prevention and control administration platform for COVID-19 provided by at least one embodiment of the present disclosure promote transformation of social administration from "extensive administration" to "fine administration" through information means, and serve a wide range of multi-level targets, and therefore, multi-level service linkage is effectively guaranteed.

For example, the public event administrating system and the big data prevention and control administration platform for COVID-19 provided by at least one embodiment of the present disclosure establish, by strengthening inspection of components and events of each grid, a supervision-handling separated form, which may timely and intuitively display data, results, etc. concerned in a law enforcement process, and therefore, screening efficiency and a risk prevention level of a front-line staff is effectively improved.

For example, the public event administrating system and the big data prevention and control administration platform for COVID-19 provided by at least one embodiment of the present disclosure perform, by docking with a professional platform, real-time broadcast of epidemic situations, and timely provide professional medical resource guidance and suggestions, and therefore, the tension of citizens can be released.

For example, the public event administrating system and the big data prevention and control administration platform for COVID-19 provided by at least one embodiment of the present disclosure may be severed as a scientific tool for anti-epidemic work, which can strengthen community prevention and control grid administration, and ensure scientific, standardized, effective and orderly development of prevention work.

For example, the public event administrating system and the big data prevention and control administration platform for COVID-19 provided by at least one embodiment of the present disclosure establish, by using the modern Internet technology, Internet of Things technology, and big data technology, a grid-based epidemic big data administration platform, which has functions of COVID-19 screening and direct reporting, telemedicine, and epidemic prevention administration, thereby a multi-level multi-module public health emergency system is created, and an informatized and digital administration mode is achieved.

For example, the public event administrating system and the big data prevention and control administration platform for COVID-19 provided by at least one embodiment of the present disclosure may implement dynamic, refined and all-round administration of each grid, monitor physical signs of personnel in the grid, and classify levels of situations, so that individuals who are highly suspected of COVID-19 may directly contact an emergency center online to acquire timely medical assistance.

For example, the public event administrating system and the big data prevention and control administration platform for COVID-19 provided by at least one embodiment of the present disclosure may be linked with an Internet of Things physical sign monitoring device, and implement data automatic uploading to present vital signs of personnel such as body temperature and blood oxygen in real time, which improves daily information collection and screening efficiency.

For example, the public event administrating system and the big data prevention and control administration platform for COVID-19 provided by at least one embodiment of the present disclosure may implement integration and sharing, interaction and interoperability between government data and social data. The big data technology is used to jointly carry out intelligent applications such as information collection and screening of migrants during a period except for the COVID-19 epidemic, and screening of susceptible population, to provide support for epidemic analysis, prevention and control, prediction and early warning.

For example, the public event administrating system and the big data prevention and control administration platform for COVID-19 provided by at least one embodiment of the present disclosure may establish a sound emergency administrating system. An effective complete system from communities, medical institutions, and emergency systems to government supervision departments is established relying on the platform, to improve the government public health emergency administrating system.

For example, the public event administrating system and the big data prevention and control administration platform for COVID-19 according to at least one embodiment of the present disclosure may implement relevant requirements of the "Healthy China Action". For example, after the COVID-19 epidemic is alleviated, the public event administrating system provided by at least one embodiment of the present disclosure may be used to monitor daily health of residents, build a big data platform for health of local residents, and assist resident health protection work.

Although the present disclosure has been described in detail with general descriptions and specific embodiments above, it will be apparent to those skilled in the art that some modifications or improvements can be made on the basis of the embodiments of the present disclosure. Therefore, these modifications or improvements made without departing from the spirit of the present disclosure belong to the scope of protection claimed in the present disclosure.

The above are only exemplary embodiments of the present disclosure and are not intended to limit the scope of protection of the present disclosure. The scope of protection of the present disclosure is determined by the appended claims.

The invention claimed is:

1. A public event administrating system, the public event involving a plurality of individuals, the administrating system comprising: a data collecting module, a data processing module, a medical resource scheduling module, and a grid administrating module, wherein the data collecting module is configured to acquire initial data about the public event from a plurality of data sources;
the data processing module is configured to process the initial data to acquire processed data; and
the public events comprises natural disasters, accident disasters, emergent public health events, and emergent social security events,
wherein the medical resource scheduling module is configured to receive an individual service request, and to allocate currently available medical resources to an individual requesting service at least according to the individual service request;
the grid administrating module is configured to divide a geographic region managed by the administrating system into a plurality of grids, and to assign a plurality of grid administrators to the plurality of grids to respectively administrate individuals in the plurality of grids;
the public event administrating further comprises an individual information declaring module,
wherein the individual information declaring module is configured to allow an accessing individual to declare individual data;
the individual data comprises at least one of the basic data, the physical condition data, the mobility data, or the contact data; and
the data collecting module is configured to acquire the individual data from the individual information declaring module as at least portion of the initial data about the public event;
the public event administrating further comprises an individual service module used in an individual terminal,
the individual service module is configured to communicate with the medical resource scheduling module to send the individual service request and establish service connections,
to communicate with the grid administrating module to allow the individual service module to communicate with a grid administrator of a grid to which it belongs; and
to communicate with an individual information declaring module to allow the individual information declaring module to collect individual data; and
the processed data includes at least one type of following data:
a list of abnormal individuals respectively belonging to the plurality of grids;
a list of individuals respectively belonging to the plurality of grids who have not declared individual data within predetermined time;
a list of individuals respectively belonging to the plurality of grids who have declared individual data within predetermined time;
a list of newly added individuals respectively belonging to each grid; a statistical result of current physical conditions of the plurality of individuals involved in the public event;
change trends of focused individuals among the plurality of individuals involved in the public event; or
a statistical result of regional distribution of the focused individuals among the plurality of individuals involved in the public event.

2. The public event administrating system according to claim 1, wherein the initial data about the public event comprises at least one of basic data, physical condition data, mobility data, or contact data of the plurality of individuals involved in the public event.

3. The public event administrating system according to claim 2, wherein the basic data comprises at least one of address, age, gender, and identity number of an individual;
the physical condition data comprises at least one of clinical symptom data, physical sign data, or diagnosis result data;
the mobility data comprises travel history data; and
the contact data comprises at least one of data on whether the individual is in contact with an individual having an abnormal physical condition or data on whether the individual is in contact with an individual having a travel history in a predetermined geographic region.

4. The public event administrating system according to claim 1, wherein the data collecting module is further configured to acquire data from at least one of an online hospital admission data source, an offline hospital admission data source, an emergency rescue platform data source, or a physical sign monitoring device data source, the acquired data is served as at least portion of the initial data about the public event.

5. The public event administrating system according to claim 4, wherein the physical sign monitoring device data source communicates with a plurality of physical sign monitoring devices; and
the plurality of physical sign monitoring devices comprise at least one of a body temperature detecting device provided in a public place, an instrument for monitoring patients provided in a hospital, or a wearable monitoring terminal.

6. The public event administrating system according to claim 1, wherein the grid administrating module comprises a grid dividing sub-module and a grid administrator sub-module;
the grid dividing sub-module is configured to divide the geographic region managed by the administrating system into the plurality of grids; and
the grid administrator sub-module is configured to establish communication with the plurality of grid administrators respectively and is configured to respectively associate the plurality of individuals in the plurality of grids with the plurality of grids and respectively associate the plurality of individuals in the plurality of grids with the plurality of grid administrators, such that the plurality of grid administrators may respectively administrate the plurality of individuals in the plurality of grids.

7. The public event administrating system according to claim 6, wherein the grid administrating module is further configured to acquire the initial data about the public event from the data collecting module, and respectively supply the initial data about the public event to corresponding grid administrators.

8. The public event administrating system according to claim 7, wherein the processed data comprises a list of abnormal individuals respectively belonging to the plurality of grids;
the abnormal individual belongs to at least one of an individual having an abnormal physical condition, an individual having a travel history in a predetermined geographic region, an individual having been in contact with an individual having an abnormal physical condition, or an individual having been in contact with an individual having a travel history in the predetermined geographic region; and
the grid administrating module is configured to acquire, from the data processing module, the list of abnormal individuals respectively belonging to the plurality of grids, and respectively supply the list of abnormal individuals respectively belonging to the plurality of grids to the plurality of grid administrators.

9. The public event administrating system according to claim 6, wherein the processed data comprises a list of abnormal individuals respectively belonging to the plurality of grids;
the abnormal individual belongs to at least one of an individual having an abnormal physical condition, an individual having a travel history in a predetermined geographic region, an individual having been in contact with an individual having an abnormal physical condition, or an individual having been in contact with an individual having a travel history in the predetermined geographic region; and
the grid administrating module is configured to acquire, from the data processing module, the list of abnormal individuals respectively belonging to the plurality of grids, and respectively supply the list of abnormal individuals respectively belonging to the plurality of grids to the plurality of grid administrators.

10. The public event administrating system according to claim 9, wherein the individual having an abnormal physical condition belongs to at least one of an individual having abnormal clinical symptom data, an individual having abnormal physical sign data, or an individual having an abnormal diagnosis result.

11. The public event administrating system according to claim 6, wherein the processed data comprises a list of individuals respectively belonging to the plurality of grids who have not declared individual data within a predetermined time;
the grid administrating module is configured to acquire, from the data processing module, the list of individuals respectively belonging to the plurality of grids who have not declared individual data within the predetermined time, and respectively supply the list of individuals respectively belonging to the plurality of grids who have not declared individual data within the predetermined time to the plurality of grid administrators.

12. The public event administrating system according to claim 6, wherein the grid administrator sub-module is further configured to respectively assign screening tasks to the plurality of grid administrators, and to acquire feedback information on the assigned screening tasks from the plurality of grid administrators.

13. The public event administrating system according to claim 6, wherein the administrating system further comprises a grid administrator terminal module used in a terminal held by each of the plurality of grid administrators; and
the grid administrator terminal module is further configured to communicate with the grid administrator sub-module, and is configured to allow each of the plurality of grid administrators to tag a specific individual in a grid administrated thereby and upload tag data.

14. The public event administrating system according to claim 6, wherein the processed data comprises at least one of a statistical result of current physical conditions of the plurality of individuals involved in the public event;
the statistical result of current physical conditions of the plurality of individuals involved in the public event comprises at least one of a statistical result of current physical sign data of the plurality of individuals involved in the public event or a statistical result of current clinical symptom data of the plurality of individuals involved in the public event; and the focused individuals belong to at least one of confirmed individuals, suspected individuals, cured individuals, dead individuals, individuals in close contact with confirmed individuals, individuals under medical observation among the individuals in close contact with confirmed individuals, or individuals released from medical observation among the individuals in close contact with confirmed individuals.

15. The public event administrating system according to claim 6, wherein the medical resource scheduling module comprises a hospital scheduling sub-module;

the hospital scheduling sub-module is configured to allocate an offline admitting hospital to the individual requesting service, or to establish a connection between the individual requesting service and a hospital supplying online service, based on positioning data of the individual requesting service, admission amount of the hospital, and a physical condition of the individual requesting service.

16. The public event administrating system according to claim 15, wherein the medical resource scheduling module further comprises an ambulance scheduling sub-module;

the hospital scheduling sub-module is configured to allocate the offline admitting hospital to the individual requesting service; and the ambulance scheduling sub-module is configured to allocate an ambulance based on positioning data of the individual requesting service, distribution situation of offline admitting hospitals and currently available ambulances.

17. The public event administrating system according to claim 15, wherein the hospital scheduling sub-module is configured to establish the connection between the individual requesting service and the hospital supplying online service; and the hospital scheduling sub-module is further configured to acquire diagnostic data of the individual requesting service and supply the diagnostic data of the individual requesting service to the data collecting module.

18. The public event administrating system according to claim 1, further comprising an information supplying module, wherein the information supplying module is configured to publish at least one of statistical results of focused individuals, protection knowledge, or rumor-refuting information; and the information supplying module is further configured to supply at least one of travel history information of confirmed individuals or medical resource information of a designated region.

19. The public event administrating system according to claim 1, wherein the processed data comprises at least one of a statistical result of current physical conditions of the plurality of individuals involved in the public event;

the statistical result of current physical conditions of the plurality of individuals involved in the public event comprises at least one of a statistical result of current physical sign data of the plurality of individuals involved in the public event or a statistical result of current clinical symptom data of the plurality of individuals involved in the public event; and the focused individuals belong to at least one of confirmed individuals, suspected individuals, cured individuals, dead individuals, individuals in close contact with confirmed individuals, individuals under medical observation among the individuals in close contact with confirmed individuals, or individuals released from medical observation among the individuals in close contact with confirmed individuals.

20. The public event administrating system according to claim 1, wherein the medical resource scheduling module comprises a hospital scheduling sub-module;

the hospital scheduling sub-module is configured to allocate an offline admitting hospital to the individual requesting service, or to establish a connection between the individual requesting service and a hospital supplying online service, based on positioning data of the individual requesting service, admission amount of the hospital, and a physical condition of the individual requesting service.

\* \* \* \* \*